United States Patent [19]

Buchholz et al.

[11] 4,281,202

[45] Jul. 28, 1981

[54] PREPARATION OF MERCAPTO-ALCOHOLS

[75] Inventors: Bernard Buchholz; Charles B. Welsh, both of Blue Bell; Henry C. Miller, Hatfield, all of Pa.

[73] Assignee: Pennwalt Corporation, Philadelphia, Pa.

[21] Appl. No.: 144,897

[22] Filed: Apr. 29, 1980

[51] Int. Cl.³ .......................................... C07C 149/18
[52] U.S. Cl. .......................................................... 568/62
[58] Field of Search ........................ 568/62, 46, 70, 71

[56] References Cited

U.S. PATENT DOCUMENTS

| | | | |
|---|---|---|---|
| 3,290,383 | 12/1966 | Pflugfelder et al. | 568/62 |
| 3,394,192 | 7/1968 | Jones | 568/62 |
| 3,574,768 | 4/1971 | Tompkins | 568/62 |

OTHER PUBLICATIONS

E. Reid, Organic Chemistry of Bivalent Sulfur, I, 378, (1958) NY, Chem. Publ. Co., Inc.

*Primary Examiner*—Donald G. Daus
*Assistant Examiner*—M. C. Eakin
*Attorney, Agent, or Firm*—John S. Munday

[57] ABSTRACT

A process for preparing mercapto-alcohols by reacting a molar excess of hydrogen sulfide with an alkylene, cycloalkylene, or aralkylene oxide in the presence of an alkali metal zeolite catalyst.

12 Claims, No Drawings

PREPARATION OF MERCAPTO-ALCOHOLS

This invention relates to the preparation of mercapto-alcohols, and, more particularly, it relates to such a preparation in the presence of a zeolite catalyst.

It is known that ethylene oxide will react with hydrogen sulfide, that the reaction is auto-catalyzed, and that excess hydrogen sulfide favors the formation of the mercapto-alcohol, 2-mercaptoethanol, over the sulfide, 2,2'-thiodiethanol.

U.S. Pat. No. 3,394,192 discloses the use of a trialkylamine as a catalyst for the reaction between hydrogen sulfide and ethylene oxide to form 2-mercaptoethanol. It also discloses the reactions of hydrogen sulfide with propylene oxide, styrene oxide, cyclohexene oxide, 3-hydroxy-1,2-propylene oxide (glycidol) and other 1,2-epoxides to produce the corresponding mercaptoalcohols.

U.S. Pat. No. 3,290,383, discloses the use of certain ion-exchange resins as catalysts for the reaction of hydrogen sulfide and alkylene oxides to produce mercapto-alcohols. The preparation of 2-mercaptoethanol by the reaction of hydrogen sulfide and ethylene oxide at 2:1 and 15:1 mol ratios is disclosed.

U.S. Pat. No. 3,574,768 discloses an improved reaction between ethylene oxide and hydrogen sulfide using as a catalyst activated alumina and a large excess of hydrogen sulfide (5 to 15 mol excess).

It is known also that, because of the uncertainty of initiation, the highly exothermic nature of the reaction, and variations in the conversion, that the auto-catalyzed reaction between hydrogen sulfide and ethylene oxide may be dangerous for batch reactions and unreliable for a continuous reaction. Several catalysts are known that overcome these difficulties and give good yields of product at mole ratios of hydrogen sulfide to ethylene oxide of about 2, at temperatures below 100° C. However, small amounts of 1,2-ethanedithiol, a highly malodorous and toxic impurity which cannot be removed by conventional distillation, are also formed with many of these catalysts. With aluminum oxide-based catalysts, for example, as much as 2% of 1,2-ethanedithiol can be formed under the preferred reaction conditions.

Triethylamine as the catalyst overcomes this objection. It gives good conversions of ethylene oxide to 2-mercaptoethanol with no 1,2-ethanedithiol by-product. This catalyst, however, is liquid. Liquid catalysts are difficult to separate and recover from the reaction product and they complicate the operations of a continuous process. It has also been learned that the product from a reaction catalyzed with triethylamine is sometimes yellow and a separate process step is required to guarantee a colorless product.

It is an object of this invention to provide an improved catalytic process for preparing mercapto-alcohols.

It is another object of this invention to provide an improved catalytic process for preparing mercapto-alcohols wherein the catalyst is a solid.

It is still another object of this invention to provide a continuous process for preparing mercapto-alcohols.

It is still another object of this invention to provide an improved process for preparing 2-mercaptoethanol without the attendant preparation of 1,2-ethanedithiol.

Still another object will appear from the more detailed description of this invention which follows:

This invention provides a process for preparing mercaptoalcohols by reacting a molar excess (i.e. above stoichiometric ratio) of hydrogen sulfide with an alkylene, cycloalkylene, or aralkylene oxide in the presence of a zeolite catalyst which is identified as Type X, Type Y, or Type L and is preferably in the sodium or potassium form. In a specific embodiment of this process the mole ratio of hydrogen sulfide to alkylene oxide is about 2:1. In a preferred embodiment of this process the reaction pressure is autogenous and the reaction temperature is 35°–120° C. In another preferred embodiment of this process the reaction is operated continuously at a temperature of 35°–120° C., a pressure sufficient to maintain the hydrogen sulfide as a liquid, the mole ratio of hydrogen sulfide to alkylene oxide being about 2:1, and the feed rate of alkylene oxide being about 300–900 gram-moles per kilogram of catalyst per 24 hours.

The process of this invention is conducted in the liquid phase, which is accomplished by conducting the reaction under pressure. In general the reaction temperature is from about 35° C. to about 120° C. The pressure is that which is sufficient to keep the hydrogen sulfide liquid. In batch reactions the autogenous pressure is sufficient for this purpose. In a continuous process, pressures of 500–1000 psig are usually sufficient.

The proportions of reactants are important in obtaining good yields of the desired product. An excess of hydrogen sulfide is necessary, but too large an excess is undesirable from an economic point of view. Generally, from 1.5 to 5.0 moles of hydrogen sulfide per mole of alkylene oxide are employed with the most desirable ratio being about 2:1.

The catalyst employed in this process is a solid zeolite. Zeolite (molecular sieve) catalysts are synthetic aluminosilicates characterized by high uniformity, well-defined pore size, large surface area, complete crystallinity and excellent reproducibility. Their structures are described in the Union Carbide Booklet F-08 entitled, "Linde Molecular Sieve Catalysts" and D. W. Breck's "Zeolite Molecular Sieves", John Wiley & Sons (1974). Various types are currently marketed by Linde (Union Carbide), Houdry (Air Products and Chemicals), Davison (W. R. Grace), Norton, and Akzo (Akzonia).

The basic structural units of synthetic zeolites are silicon and aluminum atoms tetrahedrally coordinated with four oxygen atoms. The oxygen atoms are mutually shared between tetrahedral units contributing one of the two valence charges of each oxygen atom to each tetrahedron. Since aluminum atoms are trivalent, each $AlO_4$ unit is negatively charged. The charge on these units is balanced by cations, generally sodium or potassium. These cations are exchangeable with other cations, but the sodium and potassium forms are preferred for this invention.

Although many factors influence the catalytic activity of these zeolites, the three most important are:
1. The open framework structure with its attendant pore size
2. The $SiO_2:Al_2O_3$ ratio of the framework.
3. The cations.

As in most catalytic processes, only the large-pore zeolites having pore openings in the range of 7 to 10 Angstroms are useful. The most preferred are Type X, Type Y and Type L zeolites. These are unique and specific chemical compositions, well-known to those skilled in the art, and well-defined in the above references by Union Carbide and D. W. Breck. Type X has a chemical composition expressed in terms of oxide ratios of $Na_2O:Al_2O_3:2-3SiO_2$ with a typical unit cell composition in the hydrated state of $Na_{86}[(AlO_2)_{86}(SiO_2)_{106}].264H_2O$. Type Y, on the other hand, has a composition of $Na_2O:Al_2O_3:>3-6SiO_2$. When the $SiO_2:Al_2O_3$ molar ratio is 4.8, the hydrated unit cell composition is $Na_{56}[(AlO_2)_{56}(SiO_2)_{136}].264\,H_2O$. Type L, more siliceous than Type X and Type Y, also has a pore size in the 7 to 10 Angstrom range.

An important building block of these zeolites is the sodalite cage, a truncated octahedron unit consisting of 24 $(Si,AlO_4)$ units. In Type X and Type Y the sodalite cages are connected through 4 of the 8 hexagonal faces in a tetrahedral arrangement. The pores thus created are defined by a 12-member ring of oxygen atoms, approximately 7-9 Angstroms in size, opening into a central cavity of about 11 Angstroms in diameter.

The amount of catalyst which is employed in a batch process is 10%-20% by weight of the reaction mixture of hydrogen sulfide and alkylene oxide. In a continuous process this is more conveniently translated into a rate of 300-900 gram moles of alkylene oxide per kilogram of catalyst per 24 hours.

In a batch process the product mercapto-alcohol is obtained by separating the catalyst from the reaction mixture, e.g., by filtration, and working up the liquid filtrate. When ethylene oxide is used, the crude product normally contains no malodorous 1,2-ethanedithiol and from 0.5 to 2.5% of the corresponding higher-boiling sulfide (thiodiethanol), which can be separated by distillation if desired. Thus the reaction provides a product containing at least about 95%, and frequently over 99.7% of mercapto-alcohol.

The following examples are illustrations of the process of this invention. Parts and percentages are by weight, temperatures are in degrees centigrade, and pressures are in pounds per square inch gauge unless otherwise specified. It is not intended that these examples shall limit this invention in any manner, since they are considered to be illustrations of certain embodiments of the broad invention.

L zeolite molecular sieve catalyst); the reactor was sealed, cooled with dry ice and evacuated, and then charged with 75 g. of hydrogen sulfide and 55 g. of ethylene oxide by a vapor transfer procedure. The reactor was then heated while being shaken. At about 50° C., an exotherm started and without further heating, the temperature of the autoclave rose to about 80° C. When the reaction was completed, as indicated by a dropping temperature, the unreacted hydrogen sulfide was vented and the crude product recovered. Gas chromatographic analysis of the colorless product showed it to contain 97.1% 2-mercaptoethanol, 2.5% 2,2'-thiodiethanol, and no 1,2-ethanedithiol.

EXAMPLES 2–8

In a manner similar to that of Example 1 several catalysts were evaluated in a batch process using a 300 ml stainless steel autoclave as the reactor. The results of these studies are given in Table 1. This study showed that in contrast to alumina (Examples 3, 4 and 5), certain zeolite catalysts, preferably in the sodium (Example 7) or potassium (Example 8) form, give good yields of 2-mercaptoethanol at temperatures of about 80° C., with no significant formation of undesirable 1,2-ethanedithiol. Later work (Example 10) showed that temperatures at least as high as 110° C. may be used in a continuous process without detectable dithiol formation. The only impurities in the crude product are small amounts of some much lower and much higher-boiling materials, e.g., 2,2'-thiodiethanol, which are easily separable from the 2-mercaptoethanol. The crude product analyses in Table 1 clearly show that the solid sodium and potassium zeolite catalysts are preferable to the solid alumina catalyst, in that the former avoid the formation of the difficulty separated by-product 1,2-ethanedithiol. A zeolite catalyst in the protonated form (Example 6) did not exhibit similar advantage. Triethylamine (Example 1) avoided the formation of the dithiol but this liquid catalyst promotes color-formation and it is not as suitable for use in a continuous process.

TABLE I

| Example No. | Catalyst Identification | Type | Max. Reaction Temperature | % Ethanedithiol | Crude Product Analysis % Mercaptoethanol | % Thiodiethanol |
|---|---|---|---|---|---|---|
| 2 | Triethylamine | $(C_2H_5)_3N$ liquid | 80° C. | 0.0 | 98.9 | <0.1 |
| 3 | Alcoa H-151 | $Al_2O_3$ (solid) | 80° C. | 0.46 | 98.4 | 1.1 |
| 4 | Alcoa F-1 | $Al_2O_3$ (solid) | 80° C. | 0.52 | 97.9 | 1.4 |
| 5 | Alcoa F-1 with 5%KOH | $Al_2O_3$ (solid) | 80° C. | 0.23 | 98.4 | 0.7 |
| 6 | Linde LZ-Y62 | Type Y Protonated zeolite ($NH_3$-exchanged and calcined (solid) | 70° C. | 0.24 | 97.9 | 1.4 |
| 7 | Linde LZ-Y52 | Type Y Zeolite -Na Form (solid) | 76° C. | 0.06 | 98.8 | 0.86 |
| 8 | Linde ELZ-L | Type L Zeolite -K Form (solid) | 80° C. | 0.0 | 97.1 | 2.5 |

EXAMPLE 1

A 300 ml stainless steel pressure reactor was charged with 20 g. of Linde catalyst ELZ-L (a potassium Type

EXAMPLE 9

A continuous, liquid-phase reaction was carried out by passing a mixture of hydrogen sulfide and ethylene oxide in a 2:1 to 3:1 molar ratio into a water-cooled, stainless steel reactor containing alumina catalyst. The ethylene oxide was fed at rates ranging from 153 to 480 gram-moles per kilogram of catalyst per 24-hour day. The catalyst bed was maintained at temperatures ranging from 43° C. to 85° C. and the reaction pressure was maintained at 800–900 psig by means of a backpressure control valve. The crude reaction product was found to contain 96–98% 2-mercaptoethanol by gas chromatographic analyses. 1,2-ethanedithiol appeared in the crude product when the catalyst temperature was allowed to rise above about 80° C. At 85° C., for example, there was 0.64% 1,2-ethanedithiol in the product. Maintaining the temperature below 80° C. to avoid dithiol formation was difficult, particularly at the higher throughput rates, due to the highly exothermic nature of the reaction, which generates about 30 kilocalories of heat per mole of product formed.

EXAMPLE 10

The alumina catalyst of Example 9 was replaced with a Type Y zeolite catalyst in the sodium form (Linde LZ-Y52). A continuous, liquid-phase reaction of hydrogen sulfide and ethylene oxide was carried out in the same manner as in Example 9, using the following ranges of reaction conditions:

Ethylene oxide feed-rates: 272–720 gram-moles/kg catalyst/24-hr. day
$H_2S$/ethylene oxide molar ratio: 2.1/1
Reactor pressure: 650–920 psig.
Catalyst bed temperature 40°–110° C. Gas chromatographic analysis of the crude reaction product showed it to contain 96–98% 2-mercaptoethanol and 2–3% 2,2'-thiodiethanol. With the zeolite catalyst there was no unwanted by-product 1,2-ethanedithiol detected in the crude product, even when the catalyst bed temperature was allowed to rise above 80° C. and up to 110° C. as a result of the much higher throughput rates employed (720 gram-moles at ethylene oxide per kilogram of catalyst per 24-hour day).

The zeolite catalyst thus has the important economic advantage over alumina of permitting faster throughput rates, with concomitant higher catalyst bed temperatures, to be used, without causing the unwanted by-product 1,2-ethanedithiol to appear in the product.

EXAMPLE II

In the same manner as in Example 7, hydrogen sulfide and glycidol,

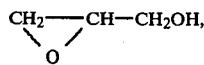

were reacted in a 4:1 molar ratio in the presence of a solid Type Y sodium zeolite catalyst (Linde LZ-Y52) in a 300 ml stainless steel autoclave. The autoclave was sealed and heated with shaking for three hours at 65° C., then cooled and vented of the excess hydrogen sulfide. Distillation gave 3-mercapto-1,2-propandiol, $HSCH_2CH(OH)CH_2OH$, as a colorless liquid (b.p. 95° C.) in 86.4% yield.

Analysis: Calculated: C, 33.3; H, 7.41; S, 29.6: Found: C, 32.4; H, 7.37; S, 29.7.

In a like manner, hydrogen sulfide can be reacted with propylene oxide, styrene oxide, or cyclohexene oxide in the presence of a sodium or potassium zeolite of the Types, X, Y, or L, to produce the corresponding mercapto-alcohol in high yield.

Although the invention has been described in considerable detail with reference to certain preferred embodiments thereof, it will be understood that variations and modifications can be effected within the spirit and scope of the invention as described hereinabove and as defined in the appended claims.

What is claimed is:

1. A process for preparing mercapto-alcohols which comprises reacting a molar excess of hydrogen sulfide at sufficient pressure to maintain said hydrogen sulfide as a liquid with an alkylene, cycloalkylene, or aralkylene oxide having up to 8 carbon atoms in the presence of a zeolite catalyst in the alkali metal form and selected from the group consisting of Type X, Type Y, Type L and mixtures thereof.

2. The process of claim 1, in which the alkali metal is sodium or potassium.

3. The process of claim 1, in which the alkylene oxide is ethylene oxide.

4. The process of claim 1, in which the alkylene oxide is propylene oxide.

5. The process of claim 1, in which the alkylene oxide is glycidol.

6. The process of claim 1, in which the cycloalkylene oxide is cyclohexene oxide.

7. The process of claim 1, in which the aralkylene oxide is styrene oxide.

8. The process of claim 1, in which the reaction pressure is autogenous and the temperature is 35°–120° C.

9. The process of claim 1, in which the mole ratio of hydrogen sulfide to alkylene oxide is about 2:1.

10. The process of claim 1 which is operated continuously and which comprises continuously feeding a mixture of hydrogen sulfide and alkylene oxide into a reaction zone containing a solid zeolite catalyst and maintained at 35°–120° C. and sufficient pressure to maintain hydrogen sulfide as a liquid, there being a molar excess of hydrogen sulfide to alkylene oxide, and the feed rate of alkylene oxide being 300–900 gram-moles per kilogram of catalyst per 24 hours; said zeolite catalyst being Type X, Type Y, or Type L and in the sodium or potassium form; and continuously recovering a product analyzing at least 95% as mercapto-alcohol.

11. The process of claim 10 in which the molar ratio of hydrogen sulfide to alkylene oxide is about 2:1.

12. The process of claim 10, in which the alkylene is ethylene oxide and the product is 2-mercaptoethanol.

* * * * *